United States Patent [19]

Forbus et al.

[11] 4,423,272

[45] Dec. 27, 1983

[54] REGENERATION OF METHANOL/METHYL ETHER CONVERSION CATALYSTS

[75] Inventors: Nancy P. Forbus, Princeton; Margaret M. Wu, Belle Mead, both of N.J.

[73] Assignee: Mobil Oil Corporation, New York, N.Y.

[21] Appl. No.: 335,797

[22] Filed: Dec. 30, 1981

[51] Int. Cl.³ .......................... C07C 1/24; C07C 1/20; B01J 29/38
[52] U.S. Cl. .................................. 585/640; 585/733; 502/53
[58] Field of Search ................ 252/411 R, 411 S, 414; 585/640

[56] References Cited

U.S. PATENT DOCUMENTS 4,144,189  3/1979  Kirkbride ....................... 252/411 R

FOREIGN PATENT DOCUMENTS 9894    4/1980  European Pat. Off. ........ 252/411 R
805830 12/1958  Britain ........................... 260/397.4

*Primary Examiner*—P. E. Konopka
*Attorney, Agent, or Firm*—A. J. McKillop; J. F. Powers, Jr.; E. F. Kenehan, Jr.

[57] ABSTRACT

A process for using hydrogen-containing gas to regenerate a zeolite catalyst comprising at least some crystalline aluminosilicate zeolitic material having pore windows formed by 8-membered rings of oxygen atoms, e.g., ZSM-34, which has been used to promote conversion of methanol and/or methyl ether to light olefins. Contact of such catalysts with hydrogen-containing gas such as hydrogen or synthesis gas at particular regeneration temperatures and pressures can restore the activity of such catalysts either in the presence or absence of organic reactants without forming potentially catalyst-damaging by-products such as water.

6 Claims, No Drawings

REGENERATION OF METHANOL/METHYL ETHER CONVERSION CATALYSTS

BACKGROUND OF THE INVENTION

1. Field of the Invention

This invention relates to a process for regenerating crystalline aluminosilicate zeolite catalysts which have been used to promote conversion of methanol and/or methyl ether to light olefins.

2. Description of the Prior Art

A remarkable growth in the production of synthetic fibers, plastics and rubber has taken place in recent decades. Such growth, to a large extent, has been supported and encouraged by an expanding supply of inexpensive petroleum raw materials such as ethylene and propylene. However, increasing demand for these light olefins has, from time to time, led to periods of shortage, either due to a diminished supply of suitable feedstocks or to limited processing capacity. In any event, it is now considered highly desirable to provide efficient means for converting raw materials other than petroleum to light olefins.

One such non-petroleum source of light olefins is coal-derived methanol and methyl ether. In this respect, it is known that methanol or methyl ether can be catalytically converted to olefin-containing hydrocarbon mixtures by contact under certain conditions with particular types of crystalline zeolite catalyst materials. U.S. Pat. No. 4,025,575, issued May 24, 1977, to Chang et al and U.S. Pat. No. 4,083,889, issued Apr. 11, 1978 to Caesar et al, for example, both disclose processes whereby methanol and/or methyl ether can be converted to an olefin-containing product over a ZSM-5 type (constraint index 1–12) zeolite catalyst. ZSM-5, in fact, converts methanol and/or methyl ether to hydrocarbons containing a relatively high concentration of light ($C_2$ and $C_3$) olefins with prolonged catalyst lifetime before catalyst regeneration becomes necessary.

It is also known that other types of zeolite catalysts can be used to convert methanol and/or methyl ether to olefin-containing hydrocarbon products containing even higher proportions of light olefins than can be realized by methanol/methyl ether conversion over ZSM-5. For example, U.S. Pat. Nos. 4,079,095 and 4,079,096, both issued Mar. 14, 1978, to Givens, Plank and Rosinski, disclose that zeolites of the erionite-offretite type, and especially ZSM-34, can usefully be employed to promote conversion of methanol and/or methyl ether to products comprising a major amount of $C_2$ and $C_3$ light olefins. However, while erionite-offretite type catalysts are highly selective to light olefins production, such smaller pore zeolites tend to age rapidly in comparison to ZSM-5 when used for methanol/methyl ether conversion.

Aged methanol/methyl ether conversion catalysts of this type can, of course, be regenerated in conventional manner by contacting the catalyst at elevated temperature with an oxygen-containing gas such as air to effect controlled burning of coke from the deactivated catalyst. While such a conventional regeneration procedure can restore catalytic activity diminished by coke formation on the catalyst during methanol/methyl ether conversion, regeneration in this manner must be conducted in the absence of organic reactants and preferably in a separate regeneration zone which is remote from the methanol/methyl ether conversion zone. Furthermore, catalyst regeneration by controlled burning of coke produces water and carbon dioxide, and water at high temperatures can permanently destroy the structure of the zeolite catalyst and thus can actually diminish catalytic activity in some instances. There is, therefore, a continuing need to develop additional catalyst regeneration procedures which can be employed to restore the diminished activity of the zeolite-based catalysts which have been used to promote the conversion of methanol and/or methyl ether to hydrocarbon products selectively enriched in light olefins.

Accordingly, it is an object of the present invention to provide an improved process for regenerating those zeolite based catalysts which promote conversion of methanol and/or methyl ether to olefin-containing products with high selectivity to production of light olefins.

It is a further object of the present invention to provide such a regeneration process wherein catalyst can be regenerated either in the presence or absence of the methanol/methyl ether organic reactants and either in or outside of the methanol/methyl ether conversion reaction zone.

It is a further object of the present invention to provide such a catalyst regeneration procedure which does not produce by-products such as water that are potentially damaging to the catalyst structure or activity.

SUMMARY OF THE INVENTION

The present invention relates to a process for regenerating a zeolite-based catalyst which has been used to promote the selective conversion of the organic reactants methanol and/or methyl ether to a hydrocarbon product rich in the light olefins such as ethylene and propylene. The catalyst employed in such a process comprises at least some crystalline aluminosilicate zeolite material characterized by a crystalline structure having pore windows formed by 8-membered rings of oxygen atoms, e.g., offretite, erionite, chabazite, Zeolite T, Zeolite W and ZSM-34. Methanol/methyl ether conversion over such a catalyst under a given set of conversion conditions tends to gradually diminish catalyst activity.

In accordance with the present invention, such catalyst activity can be restored, either in the presence or in the substantial absence of organic reactants, by contacting the catalyst with hydrogen-containing gas under regeneration conditions which include a regeneration temperature of from about 200° C. to 600° C., and a regeneration pressure of from about 50 psig to 700 psig.

DETAILED DESCRIPTION OF THE INVENTION

Methanol and/or methyl ether can be converted to hydrocarbons by contacting such reactants with a particular type of crystalline aluminosilicate zeolite catalyst material. Such zeolites have a crystal structure that provides constrained access to, and egress from, the intracrystalline free space by virtue of having a pore dimension which is usually greater than about 3.6×3.7 Angstroms. Such zeolites also generally have a Constraint Index substantially greater than 12. Zeolitic material of this type has pore windows of about the size such as would be provided by 8-membered rings of oxygen atoms. It is to be understood that these rings are those formed by the regular disposition of the tetrahedra making up the anionic framework of the crystalline aluminosilicate zeolite, the oxygen atoms themselves being bonded to silicon (or aluminum) atoms at the centers of the tetrahedra.

It should also be understood that the zeolites useful herein include zeolite types which may contain some crystalline zeolitic material having pore windows of a size formed by oxygem atom rings containing more than 8 members. For example, a number of natural and synthetic zeolites are known to comprise intergrowths of more than one type of crystalline material. Thus, a given zeolite may contain some crystalline material which has pore windows formed by 8-membered rings of oxygen atoms and some material having pore windows formed by 10 or 12 membered rings. The zeolites employed in the regeneration process of the instant invention are those which have at least a portion of their total crystalline zeolitic material composed of zeolite material having pore windows formed by 8-membered rings of oxygen atoms.

Zeolites which comprise at least some of the 8-membered ring crystalline zeolite material include those of the erionite-offretite family such as synthetic and natural erionite, synthetic and natural offretite, Zeolite T, Zeolite W, natural and synthetic chabazite and ZSM-34. Chabazite, erionite and offretite are all more particularly described in Meier and Olson, *Atlas of Zeolite Structure Types,* published in 1978 by the International Zeolite Association and the references cited therein. Zeolite T is described in U.S. Pat. No. No. 2,950,952 and Zeolite W is described in U.S. Pat. No. 3,012,853. All of these publications and patents are incorporated herein by reference.

A particularly preferred zeolite material for use in the regeneration process of the present invention is ZSM-34. ZSM-34 and its synthesis are more fully described in Rubin et al; U.S. Pat. No. 4,116,813, issued Sept. 26, 1978 and its parent U.S. Pat. No. 4,086,186, issued Apr. 25, 1978. These patents are also incorporated herein by reference ZSM-34 is a unique crystalline aluminosilicate zeolite, belonging to the erionite-offretite family, having the composition, as synthesized, and after drying of:

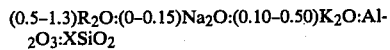

$$(0.5-1.3)R_2O:(0-0.15)Na_2O:(0.10-0.50)K_2O:Al_2O_3:XSiO_2$$

where R is the organic nitrogen-containing cation derived from choline [$(CH_3)_3NCH_2CH_2OH$] and X is 8 to 50, preferably 8 to 30 and still more preferably 8 to 20. This zeolite, unlike other members of the erionite-offretite family, appears to have a tubular morphology and the capability, after calcination at 1000° F. for at least a period of time to remove the organic cation, of sorbing at least 9.5 weight percent of n-hexane, at ambient temperature and a n-hexane pressure of 20 mm. which is higher than that for any other known offretite or erionite. ZSM-34 is characterized by the X-ray powder diffraction pattern as set forth in the aforementioned U.S. Pat. Nos. 4,116,813 and 4,086,186.

All of the foregoing zeolites, as synthesized, may be calcined to remove the organic constituent ($R_2O$) and/or ion exchanged to replace the alkali metal ions with hydrogen ion precursor, e.g. ammonium, and/or other metal ions, particularly metals from Groups IB, IIA, IIB, IIIB, VIIA, VIII and the rare earth metals with only minor changes in the X-ray characterization and sorption properties. The ion exchanged products are catalytically active zeolites useful in the process of this invention.

In conducting methanol/methyl ether conversion and subsequent catalyst regeneration in accordance with the present invention, it may be desirable to incorporate the above-described crystalline aluminosilicate zeolites in another material resistant to the temperature and other conditions employed in the process. Such matrix materials include synthetic or naturally occurring substances as well as inorganic materials such as clay, silica and/or metal oxides. The latter may be either naturally occuring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the small pore zeolites employed herein may be compound with a porous matrix material, such as alumina, silica-alumina, silica-magnesia, silica-zirconia, silica-thoria, silica-beryllia, silica-titania, as well as ternary combinations, such as silica-alumina-thoria, silica-alumina-zirconia, silica-alumina-magnesia and silica-magnesia zirconia. The matrix may be in the form of a cogel. The relative proportions of finely divided zeolite and inorganic oxide gel matrix may vary widely with the zeolite content ranging from between about 1 to about 99 percent by weight and more usually in the range of about 5 to about 80 percent by weight of the composite.

The process of the instant invention involves regeneration of the above-described catalyst compositions after such catalysts have been utilized to promote the selective conversion of methanol and/or methyl ether to hydrocarbons, particularly light ($C_2$–$C_3$) olefins. Conversion processes of this type are described more fully in U.S. Pat. Nos. 4,079,095 and 4,079,096, and disclosures of which are incorporated herein by reference.

In accordance with such conversion processes, a chargestock comprising methanol (methyl alcohol), methyl ether, methanol/methyl ether mixtures or mixtures of such organic reactants with water can be contacted in the vapor phase with the particular catalyst materials hereinbefore described in a reaction zone and under reaction conditions suitable for effecting conversion of methanol and/or methyl ether to olefins. When water is employed along with the organic feed, the amount of water fed with the organic charge of methanol and/or dimethyl ether can be generally at least about 0.25 moles of water per mole of the organic reactants. Preferably, the amount of water added can be greater than about 0.5 moles of water per mole of organic rectants. The amount of water initially added to the organic charge usually will not exceed about 40 moles per mole of said charge.

Reaction conditions employed in the methanol/methyl ether conversion to hydrocarbons involve both elevated temperatures and pressures in the conversion reaction zone. Thus, such conditions include an operating temperature between about 200° C. and 500° C., preferably 300° C. and 450° C., a pressure between about 50 psig (345 kPa) and 500 psig (3447 kPa), preferably about 100 psig (689 kPa) and 250 psig (1724 kPa); and a weight hourly space velocity (WHSV) of the organic reactants of between about 0.05 and 30, preferably about 0.1 and 10.

In a preferred embodiment, the organic reactants are introduced to the reaction zone along with a gaseous carrier or diluent which can be, for example, hydrogen, nitrogen, carbon monoxide, carbon dioxide or mixtures thereof such as synthesis gas. Hydrogen-containing gas such as hydrogen or synthesis gas are the preferred diluents. Hydrogen-containing gaseous diluents can prolong catalyst lifetime for methanol/methyl ether conversion processes of the type herein involved. Processes employing gaseous diluents of this type are described more fully in the concurrently filed, abandoned U.S. patent application of Forbus and Wu, having Ser. No. 335,796. When such a diluent is employed, the weight hourly space velocity of the diluent can range from about 0.003 to 20 and the molar ratio of diluent to organic reactants can range from about 0.5:1 to 40:1.

The methyl alcohol and/or methyl ether conversion procedure described herein may be carried out as a batch-type, semi-continuous or continuous operation utilizing a fixed, fluidized or moving bed catalyst system. A preferred embodiment entails use of a catalyst zone wherein the alcohol or ether charge together with gaseous diluent and optionally with added water is passed concurrently or countercurrently through a fluidized or moving bed of particle-form catalyst. The product stream in the conversion process contains steam and a hydrocarbon mixture of paraffins and olefins, substantially devoid of aromatics. This mixture is particularly rich in light olefins, e.g., ethylene and propylene. Generally, a major fraction of the total olefins is ethylene plus propylene with the ethylene content of the product exceeding the propylene content. Thus, the predominant hydrocarbon product constitutes valuable petrochemicals. The steam and hydrocarbon products may be separated from one another by methods well known in the art. In a preferred embodiment of the invention, the unconverted methanol and/or methyl ether, as well as at least part of the water in the product, can be recycled to the reaction zone.

In accordance with the present invention, a procedure is provided for regenerating the hereinbefore described catalyst compositions after the activity of such a catalyst has been diminished by virtue of its use in the methanol/methyl ether conversion processes also as hereinbefore described. Such a procedure involves contacting the aged conversion catalyst with hydrogen-containing gas under particular catalyst regeneration conditions. The hydrogen-containing gas employed in the regeneration procedure preferably comprises substantially pure hydrogen.

Hydrogen-containing regeneration gas can also comprise mixtures of hydrogen with other inert gaseous diluents such as carbon monoxide, carbon dioxide, nitrogen and the like. One suitable mixture of gases for use as the hydrogen-containing regeneration gas comprises mixtures of hydrogen and carbon monoxide such as are found in synthesis gas from petroleum or coal processing. Synthesis gas frequently comprises a mixture of various gases such as hydrogen, carbon monoxide, carbon dioxide, methane, nitrogen, carbonyl sulfide, carbon disulfide, ammonia, hydrogen sulfide, etc. Such synthesis gas may be derived from fossil fuel conversion by any of the known conversion and gasification methods. Th term "fossil fuels", as used herein, is intended to include anthracite and bituminous coal, lignite, crude petroleum, shale oil, oil from tar sands, natural gas, as well as fuels derived from simple physical separations or more profound transformations of these materials, including coked coal, petroleum coke, gas oil, residua from petroleum distillation, and two or more of any of the foregoing materials in combination. Other carbonaceous fuels such as peat, wood, and cellulosic waste materials also may be used.

Processes for the conversion of coal and other hydrocarbons such as natural gas to a gaseous mixture consisting essentially of hydrogen and carbon monoxide, or of hydrogen and carbon monoxide and carbon dioxide, are well known. Although various processes may be employed for the gasification, those of major importance depend either on the partial combustion of the fuel with an oxygen-containing gas or on the high temperature reaction of the fuel with steam, or on a combination of these two reactions. Such gasification processes include in-situ gasification schemes, such as the underground partial combustion of coal and petroleum deposits. An excellent summary of the art of gas manufacturing, including synthesis gas useful herein, from solid and liquid fuels, is given in ENCYCLOPEDIA OF CHEMICAL TECHNOLOGY, Edited by Kirk-Othmer, Second Edition, Volumn 10, pages 353–433 (1966), Interscience Publishers, New York, N.Y., the contents of which are herein incorporated by reference.

The raw synthesis gas produced from fossil fuels will contain various impurities such as particulates, sulfur compounds, and metal carbonyl compounds, and will be characterized by a hydrogen-to-carbon oxides ratio which will depend on the fossil fuel and the particular gasification technology utilized. Such raw syngas is generally purified before being used as the hydrogen-containing regeneration gas in the catalyst regeneration process of the present invention. In such cases, the hydrogen-containing gas can comprise mixtures of hydrogen and carbon monoxide in a molar ratio of hydrogen to carbon monoxide of from 0.2:1 to 10:1, more preferably from about 0.5:1 to 3:1.

The catalyst regeneration conditions employed in the present invention include a regeneration temperature of from about 200° C. to 600° C., more preferably from about 300° C. to 500° C. and a regeneration pressure of from about 50 psig (345 kPa) to 700 psig (4826 kPa), more preferably from about 100 psig (689 kPa) to 500 psig (3447 kPa). Regeneration may be carried out by conducting the aged catalyst to a separate regeneration zone for contact with hydrogen-containing gas, after which the regenerated catalyst can be recycled to the conversion zone for further contact with the methanol and/or methyl ether containing feed. Alternatively, the aged catalyst can be regenerated in the reaction zone itself by controlled contact with hydrogen-containing gas under the regeneration conditions of the present invention.

In one embodiment of the present invention, catalyst can be regenerated by contacting the catalyst with hydrogen-containing gas under the hereinbefore described regeneration conditions in the substantial absence of the organic reactants during such regeneration. When a hydrogen-containing diluent is used in the methanol/methyl ether conversion procedure, regeneration in this manner can conveniently be accomplished by simply discontinuing the flow of organic reactants fed to the reaction zone while allowing flow of hydrogen-containing diluent to continue into the reaction zone under conditions effective to bring about the desired catalyst regeneration.

Regeneration of the methanol/methyl ether conversion catalyst can also be carried out in accordance with the present invention in the presence of the organic reactants used in the conversion reaction. Regeneration of this type can be effected by adding hydrogen-containing gas to the reactant-containing feedstream introduced into the reaction zone or by increasing pressure in the reaction zone which already contains the organic reactants and hydrogen-containing gas being used as a diluent. To bring about restoration of diminished catalytic activity in such instances where hydrogen is already present during the methanol/methyl ether conversion reaction, it is generally necessary to contact catalyst with hydrogen-containing gas at a regeneration pressure which exceeds the elevated pressure of the methanol/methyl ether conversion conditions existing in the reaction zone immediately prior to catalyst regeneration.

Catalyst regeneration using hydrogen-containing gas in the manner described produces no water or carbon dioxide as by-products of the regeneration procedure. Regeneration can thus be effected without the possibility of forming potentially catalyst damaging amounts of water. The following examples will serve to illustrate the regeneration process of this invention without limiting the same.

EXAMPLE I

ZSM-34 is prepared by interacting the following solutions:
A. Caustic Aluminate
    68.89 grams sodium aluminate (20 wt. % Na, 43.1 wt. % $Al_2O_3$, Balance $H_2O$)
    29.28 grams NaOH (77.5 wt. % $Na_2O$)
    26.4 grams KOH 86.4% KOH
    540 grams $H_2O$
B. Silica Solution
    780 grams Colloidal Silica sol (30 Wt. % $SiO_2$)
C. Choline Chloride
    228 grams These are mixed together in a 2 liter autoclave adding solution C to solution A and then adding solution B followed by a 15 minute continuous mixing. The autoclave is then sealed, pressure-tested and then heated to and held at 300° F. for 8 days. The contents are stirred continuously during the 8 day crystallization period.

The autoclave and its contents are cooled to room temperature, and the crystalline product is filtered and washed. On analysis the product is found to contain:
Na, wt %: 0.68
K, wt %: 3.59
$Al_2O_3$ wt %: 13.5
$SiO_2$, wt %: 78.5
N, wt %: 2.5

The resulting ZSM-34 product has the following molar composition:

$$0.54\ R_O:0.11\ Na_2O:0.35\ K_2O:Al_2O_3:9.87\ SiO_2$$

A sample of the calcined alkali ZSM-34 is further processed by contacting with a 10 wt % $NH_4Cl$ solution for 1 hour at about 185° F. using 10 ml. of solution for each gram of ZSM-34. A total of four contacts are made at these conditions followed by final filtration and water washing essentially free of chloride ion.

The product is dried at 230° F. and calcined for 10 hours at 1000° F. The residual alkali content as Na is 0.035 wt. % while the residual K content is 1.47 wt. %. This product has a surface area of 517 $m^2/g$ and the following sorption capacity:
Cyclohexane, wt %: 2.6
n-Hexane, wt %: 10.0
$H_2O$, wt %: 18.7

EXAMPLE II

ZSM-34 prepared in a manner similar to that described in Example I and back-exchanged with ammonium chloride to convert it to the ammonium form is used in a continuous series of runs to convert methanol to hydrocarbons, followed by the catalyst regeneration procedures of the present invention. The $NH_4$ ZSM-34 zeolite employed in such testing has a surface area of 475 $m^2/g$ and the following sorption capacity:
Cyclohexane, wt. %: 4.5
n-Hexane, wt. 90%: 9.9
$H_2O$, wt. %: 16.5

In the conversion and regeneration procedure, two grams of $NH_4$ZSM-34 of 14/20 mesh size and diluted with 4 g quartz chips are packed into a reactor for methanol to ethylene conversion under pressure of hydrogen. After 72 hours on stream for methanol reaction under various temperatures and pressures, the reaction conditions are set at 100 psi, 365° C. with hydrogen feed rate at 100 cc/min and methanol at 1 cc/hr or 2 cc/hr. These results are summarized in Table IA. In these runs, the selectivities to ethylene and total light olefins are high, the methanol conversion to hydrocarbons is low. The methanol feed is then discontinued. Only hydrogen gas is fed through the catalyst for regeneration. Hydrogen feed rate is 100 cc/min. Reactor temperature is maintained at 400° C. and reactor pressure at 100 psig.

After the regeneration, reactor conditions are returned to 100 psig, 370° C. with hydrogen feed stock rate at 100 cc/min and methanol at 1 cc/hr. The results of such methanol conversion to hydrocarbons subsequent to regeneration are summarized in Table IB.

TABLE IA

METHANOL CONVERSION TO LIGHT OLEFINS BY $NH_4$ZSM-34
FOLLOWED BY HYDROGEN REGENERATION OF CATALYST

| Reaction Conditions Before $H_2$ Regeneration | Time on Stream (hrs) | % $CH_3OH$ Conv. | Wt. % Selectivity | | | | | |
|---|---|---|---|---|---|---|---|---|
| | | | $CH_4$ | $C_2H_6$ | $C_2H_4$ | $C_3H_8$ | $C_3H_6$ | $C_2\!=\!-C_4\!=$ |
| 100 psi, 365° C. | 73.50 | 31.70 | 7.10 | 4.40 | 57.20 | 1.50 | 23.50 | 80.70 |
| $H_2$, 100 cc/min | 74.50 | 30.60 | 6.90 | 4.40 | 56.80 | 1.40 | 23.70 | 80.50 |
| MeOH, cc/hr | 75.50 | 34.30 | 6.70 | 4.40 | 58.20 | 1.50 | 23.00 | 81.20 |
| | 92.50 | 53.80 | 6.10 | 4.10 | 57.90 | 1.90 | 24.40 | 82.30 |
| | 95.50 | 47.00 | 6.40 | 4.00 | 58.10 | 1.50 | 24.00 | 82.10 |
| | 97.50 | 43.60 | 6.90 | 4.20 | 56.90 | 1.40 | 24.00 | 80.90 |
| 100 psi, 365° C. | 117.50 | 21.00 | 8.60 | 3.90 | 48.60 | 1.00 | 26.00 | 74.60 |
| $H_2$, 100 cc/min | 142.00 | 21.10 | 8.70 | 4.40 | 47.60 | 1.00 | 26.30 | 73.90 |

TABLE IA-continued

METHANOL CONVERSION TO LIGHT OLEFINS BY NH₄ZSM-34 FOLLOWED BY HYDROGEN REGENERATION OF CATALYST

| Reaction Conditions Before H$_2$ Regeneration | Time on Stream (hrs) | % CH$_3$OH Conv. | CH$_4$ | C$_2$H$_6$ | C$_2$H$_4$ | C$_3$H$_8$ | C$_3$H$_6$ | C$_2$=—C$_4$= |
|---|---|---|---|---|---|---|---|---|
| MeOH, 2 cc/hr | 162.00 | 22.00 | 8.90 | 5.20 | 46.60 | 1.10 | 26.10 | 72.70 |

After 162 hours on stream catalyst is regenerated with H$_2$ at 400° C., 100 psig. H$_2$ = 100 cc/hr for 18 hours.

TABLE IB

METHANOL CONVERSION TO LIGHT OLEFINS BY NH₄ZSM-34 AFTER HYDROGEN REGENERATION OF CATALYST

| Reaction Conditions After H$_2$ Regeneration | Time on Stream (hrs)[1] | % CH$_3$OH Conv. | CH$_4$ | C$_2$H$_6$ | C$_2$H$_4$ | C$_3$H$_8$ | C$_3$H$_6$ | C$_2$=—C$_4$= |
|---|---|---|---|---|---|---|---|---|
| 100 psi, 370° C. | 2.7 | 98.3 | 5.8 | 7 | 35 | 8.1 | 22.4 | 68.3 |
| H$_2$, 100 cc/min | 3.3 | 97.3 | 5.5 | 6.6 | 45.9 | 4.8 | 25.2 | 77.8 |
| MeOH, 1 cc/hr | 3.9 | 87.7 | 5.4 | 6.2 | 51.2 | 3.7 | 26.4 | 82.3 |
| | 4.5 | 77.1 | 5.7 | 6.7 | 52.7 | 3.3 | 26.5 | 83 |
| | 5 | 70.3 | 5.8 | 7.1 | 53.2 | 3.2 | 26.2 | 82.7 |
| | 6 | 63.7 | 5.8 | 7 | 54.3 | 2.9 | 26 | 83.2 |
| | 6.9 | 57.9 | 6 | 7.2 | 55.3 | 2.7 | 25.4 | 83.2 |
| | 7.9 | 55 | 6 | 7.2 | 55.9 | 2.6 | 25.1 | 83.3 |
| | 9.9 | 50.9 | 6 | 7 | 57.4 | 2.3 | 24.4 | 83.9 |
| | 12 | 46.9 | 5.9 | 6.3 | 59.2 | 2 | 23.9 | 85 |
| | 13.9 | 42.1 | 6.2 | 6.1 | 60 | 1.6 | 23.4 | 85.3 |
| | 15.9 | 39.8 | 6.5 | 6.1 | 59.9 | 1.5 | 23.3 | 85.1 |
| | 17.9 | 35.4 | 7 | 6.1 | 59.3 | 1.3 | 23.5 | 84.8 |
| | 20 | 33.6 | 7.1 | 5.8 | 59.2 | 1.2 | 23.8 | 85.1 |
| | 21.9 | 37.3 | 8.2 | 8.3 | 52.3 | 1.8 | 25.5 | 80.4 |

[1]Time on stream after regeneration

The Tables IA and IB data demonstrate that treatment of the aged catalyst with hydrogen promotes catalytic activity to the same levels as original fresh catalyst for conversion of methanol to a light olefin-enriched hydrocarbon product.

EXAMPLE III

Another continuous series of runs employing NH₄ZSM-34 zeolite catalyst is carried out in order to convert an anhydrous methanol feed to hydrocarbon product in the presence of hydrogen and with hydrogen regeneration of the catalyst. Various reaction conditions are employed for the runs up to 184 hours on stream after which time the catalyst is regenerated in the absence of organic reactants. Additional runs are then carried out with variation in hydrogen pressure. Reaction conditions, methanol conversion and light olefins selectively for each run are set forth in Table II.

TABLE II

METHANOL CONVERSION OVER ZSM-34 WITH HYDROGEN TREATMENT TO REGENERATE CATALYST

| | | | | | | | | | Catalyst is regenerated by H$_2$ overnight at 350° C., 100 psig, 100 cc/min | | | |
|---|---|---|---|---|---|---|---|---|---|---|---|---|
| Run No. | 1 | 2 | 3 | 4 | 5 | 6 | 7 | 8 | 9 | 10 | 11 | 12 |
| Total time on Stream (hrs) | 2 | 24 | 44 | 71 | 91 | 94 | 120 | 184 | 25 | 80 | 125 | 167 |
| Temperature, °C. | 394 | 394 | 380 | 370 | 370 | 365 | 365 | 365 | 370 | 370 | 370 | 370 |
| Pressure, psig | 500 | 250 | 250 | 250 | 250 | 100 | 100 | 100 | 100 | 200 | 150 | 125 |
| WHSV: H$_2$ | 0.2 | 0.2 | 0.2 | 0.2 | 0.1 | 0.1 | 0.2 | 0.2 | 0.2 | 0.2 | 0.2 | 0.2 |
| MeOH | 0.4 | 0.4 | 0.4 | 0.4 | 0.4 | 0.4 | 0.4 | 0.8 | 0.4 | 0.4 | 0.4 | 0.4 |
| MeOH Conversion, %*** | 100 | 100 | 98 | 66 | 54 | 38 | 41 | 21 | 50** | 70 | 61 | 54 |
| Wt % Selectivity | | | | | | | | | | | | |
| C$_2$H$_4$ | 10 | 33** | 28 | 41 | 43 | 57 | 57 | 49 | 58 | 40 | 48 | 50 |
| C$_3$H$_6$ | 13 | 21 | 27 | 24 | 24 | 24 | 24 | 26 | 25 | 25 | 25 | 25 |
| C$_4$H$_8$ | 12.0 | 10 | 0 | 1 | 0 | 0 | 0 | 0 | 0 | 0 | 2 | 4 |
| CH$_4$ | 10.0 | 11 | 7 | 10 | 12 | 7 | 7 | 9 | 7 | 14 | 11 | 10 |
| C$_2$H$_6$ | 18 | —* | 11 | 10 | 10 | 5 | 4 | 4 | 7 | 13 | 10 | 10 |
| C$_3$H$_8$ | 34.0 | 19 | 15 | 10 | 5 | 3 | 1 | 1 | 2 | 8 | 5 | 2 |
| Others | 3 | 6 | 12 | 4 | 6 | 4 | 7 | 11 | 1 | 0 | 0 | 0 |
| Total C$_2$–C$_4$ = | 35.0 | — | 55 | 66 | 67 | 81 | 81 | 75 | 83 | 65 | 75 | 80 |

*C$_2$*, C$_2$ = were not separated.
**Methanol conversion never reached a steady state under this set of conditions.
***To hydrocarbons The Table II data demonstrate that aged methanol conversion catalyst can be regenerated with hydrogen under regeneration conditions by simple cutting off the methanol feed. In Table II, between Runs 8 and 9, the catalyst was regenerated with $H_2$ for 16 hours. When the methanol feed was restarted, the catalyst was active for methanol conversion, and the original selectivities to ethylene and light olefins were restored.

The Table II data also show that the aged catalyst can be continuously regenerated during the methanol conversion reaction by increasing hydrogen pressure. This was demonstrated in Runs 9 and 10. Under the conditions shown in Run 9, the catalyst continuously aged over a period of 20 hours. At the end of this time, methanol conversion was only 33%. The reactor pressure was then raised from 100 psig to 200 psig. The methanol conversion gradually increased to ~70% after five hours on stream with the new conditions.

What is claimed is:

1. In a process whereby the organic reactants methanol and/or methyl ether ar catalytically converted in the vapor phase to a hydrocarbon product rich in ethylene and propylene in a reaction zone under conversion conditions including elevated temperature and pressure and in the presence of a catalyst comprising a crystalline aluminosilicate zeolite material characterized by a crystalline structure having pore windows formed by 8-membered rings of oxygen atoms, the improvement which comprises:

effecting regeneration of said catalyst, to restore catalytic activity diminished during conversion of the organic reactants, by contacting said catalyst with hydrogen-containing gas in the reaction zone, in the presence of said vapor phase organic reactants and at a regeneration pressure which exceeds the elevated pressure of the conversion conditions existing in said reaction zone immediately prior to said catalyst regeneration and at a regeneration temperature of from about 200° C. to 600° C. and a regeneration pressure of from about 50 to 700 psig.

2. A process according to claim 1 wherein said regeneration temperature ranges from about 300° C. to 500° C. and said regeneration pressure ranges from about 100 psig to 500 psig.

3. A process according to claim 2 wherein said zeolite material is selected from erionite, offretite, chabazite, Zeolite T, Zeolite W and ZSM-34.

4. A process according to claim 3 wherein the organic reactants are converted in the presence of a hydrogen-containing diluent and under conversion conditions which include a temperature of from about 200° C. to 500° C., a reaction zone pressure from about 50 psig to 500 psig, and a weight hourly space velocity of the organic reactants of from about 0.05 to 30.

5. A process according to claim 4 wherein said zeolite is ZSM-34.

6. A process according to claim 5 wherein the weight hourly space velocity of the hydrogen-containing diluent ranges from about 0.003 to 20 and the molar ratio of hydrogen-containing diluent to organic reactants ranges from about 0.5:1 to 40:1.

* * * * *

UNITED STATES PATENT AND TRADEMARK OFFICE
CERTIFICATE OF CORRECTION

PATENT NO. : 4,423,272

DATED : December 27, 1983

INVENTOR(S) : Nancy P. Forbus and Margaret M. Wu

It is certified that error appears in the above-identified patent and that said Letters Patent is hereby corrected as shown below:

Col. 3, line 6, "oxygem" should be --oxygen--.

Col. 3, line 28, "No. No." should be --No.--.

Col. 3, line 50, "tubular" should be --tabular--.

Col. 4, line 22, "compound" should be --compounded--.

Col. 4, line 28, "silica-magnesia zirconia" should be --silica-magnesia-zirconia--.

Col. 6, line 38, "of from" should be --of from about--.

Col. 8, line 5, "0.54$R_0$:" should be --0.54$R_2O$:--.

Col. 10, line 40, "selectively" should be --selectivity--.

Col. 11, line 21, "ar" should be --are--.

Signed and Sealed this

Nineteenth Day of February 1985

[SEAL]

Attest:

DONALD J. QUIGG

Attesting Officer

Acting Commissioner of Patents and Trademarks